United States Patent [19]
Mercat

[11] Patent Number: 4,811,612
[45] Date of Patent: Mar. 14, 1989

[54] METHOD AND DEVICE FOR MEASURING THE TORQUE TRANSMITTED BY THE DRIVING WHEEL OF A CYCLE AND A CYCLE EQUIPPED WITH SAID DEVICE

[75] Inventor: Jean-Pierre Mercat, Chateau-enault, France

[73] Assignee: Ste Look, Nevers, France

[21] Appl. No.: 121,144

[22] Filed: Nov. 16, 1987

[30] Foreign Application Priority Data

Nov. 19, 1986 [FR] France ............... 86 16109

[51] Int. Cl.⁴ .............................................. G01L 3/14
[52] U.S. Cl. .................................................. 73/862.34
[58] Field of Search ........... 73/862.34, 862.33, 862.32, 73/862.28

[56] References Cited

U.S. PATENT DOCUMENTS

| | | | |
|---|---|---|---|
| 3,298,223 | 1/1967 | Dyer, Jr. ................ | 73/862.33 X |
| 4,345,481 | 8/1982 | Schroyer ................ | 73/862.34 |
| 4,592,241 | 6/1986 | Obayashi et al. ........ | 73/862.34 |

FOREIGN PATENT DOCUMENTS 3150149 6/1983 Fed. Rep. of Germany .
2394790 1/1979 France .
59-69541 4/1984 Japan .

OTHER PUBLICATIONS

"Digital Speedometer and Crank Position Indicator for the Monark Bicycle Ergometer", *Proceedings of the IEEE 1982 National Aerospace and Electronics Conference*, By D. B. Reynolds, vol. 1, p. 194.

*Primary Examiner*—Charles A. Ruehl
*Attorney, Agent, or Firm*—Young & Thompson

[57] ABSTRACT

The driving wheel of a bicycle or moped is fitted with radial spokes for ready detection of angular divergence between hub and rim under the action of torque. The angular position of the hub is detected by means of a perforated disk having openings which pass in front of a photoelectric sensor. A hoop attached to the rim is provided with rectangular notches which also pass in front of a photoelectric sensor. The signals produced by the sensors are sent to an electronic unit for computing the torque from the time interval by which the hoop lags with respect to the disk. In addition, detection of the passage of disk openings serves to calculate the speed which is displayed together with the power obtained by electronic multiplication of the torque by the speed.

10 Claims, 4 Drawing Sheets

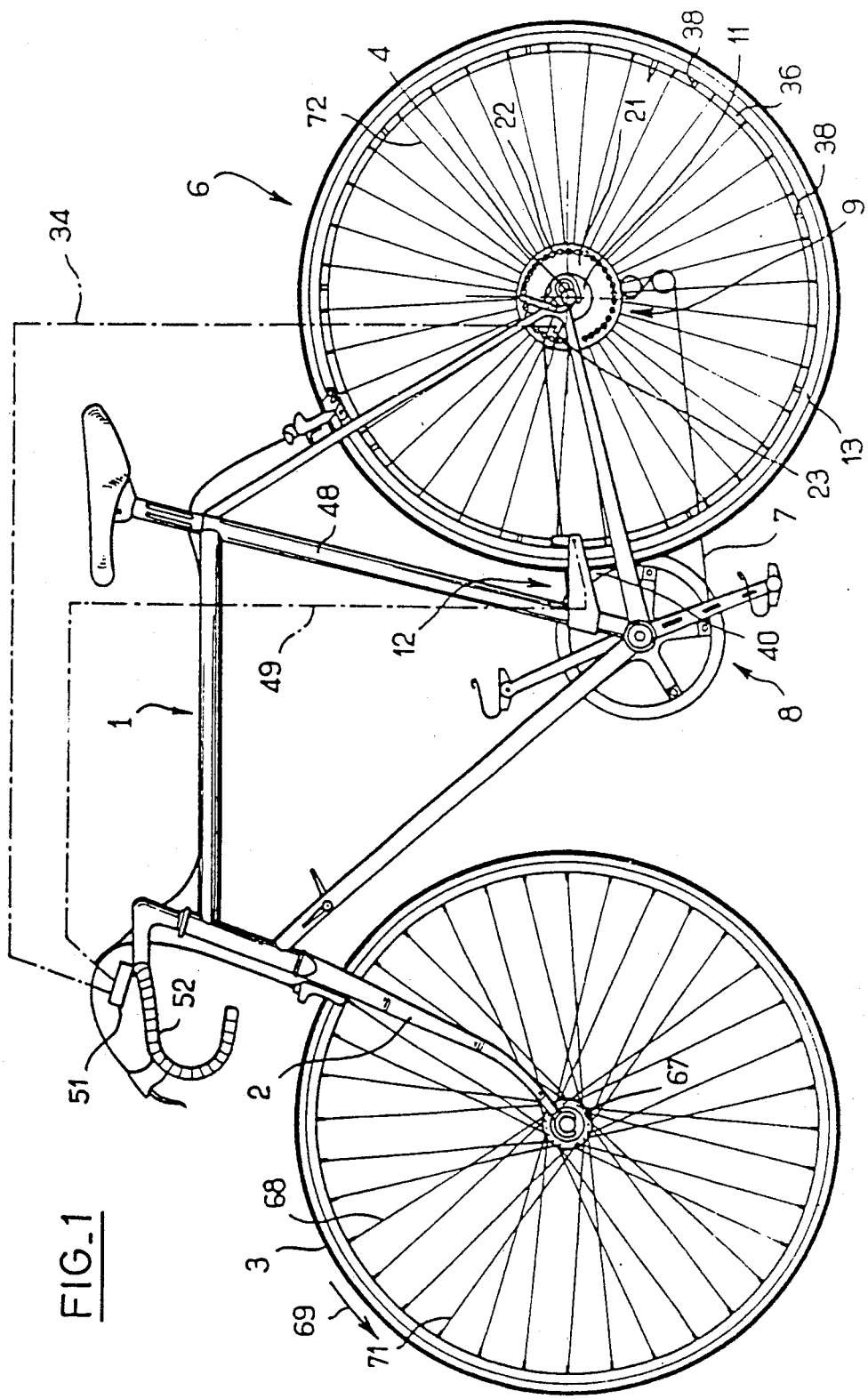
FIG_1

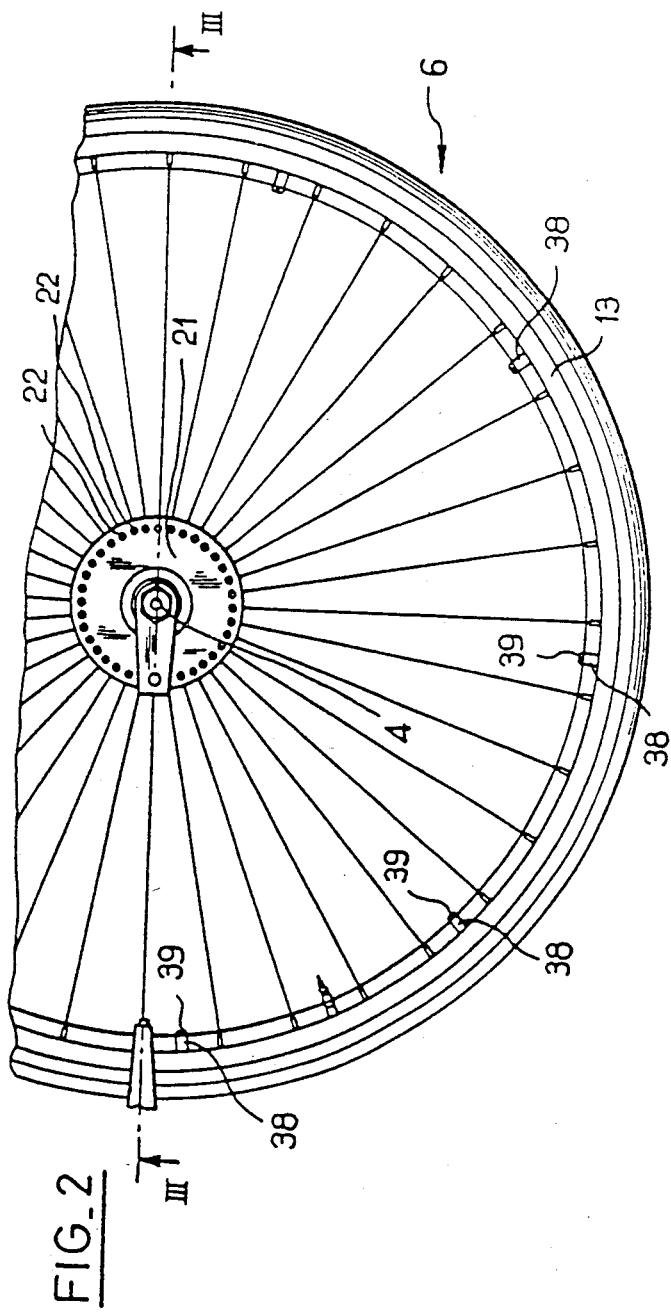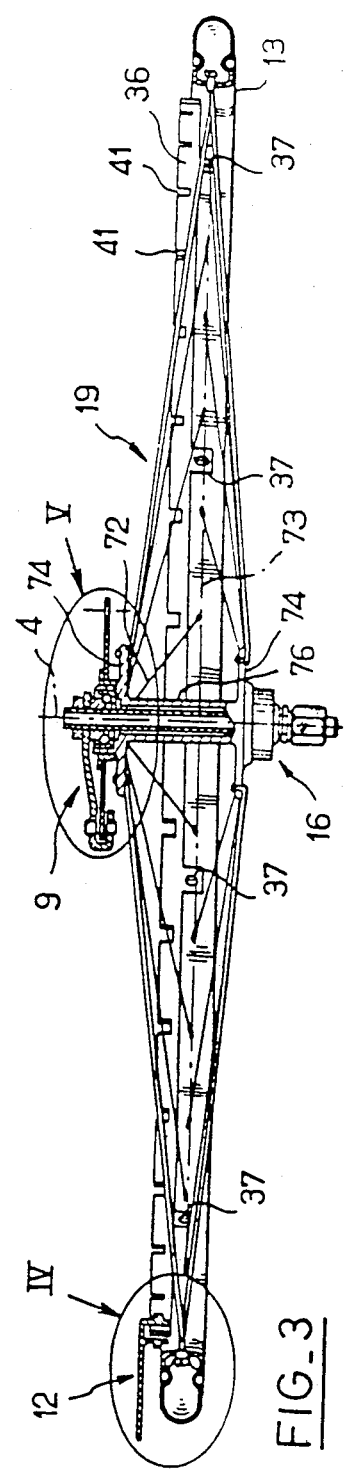

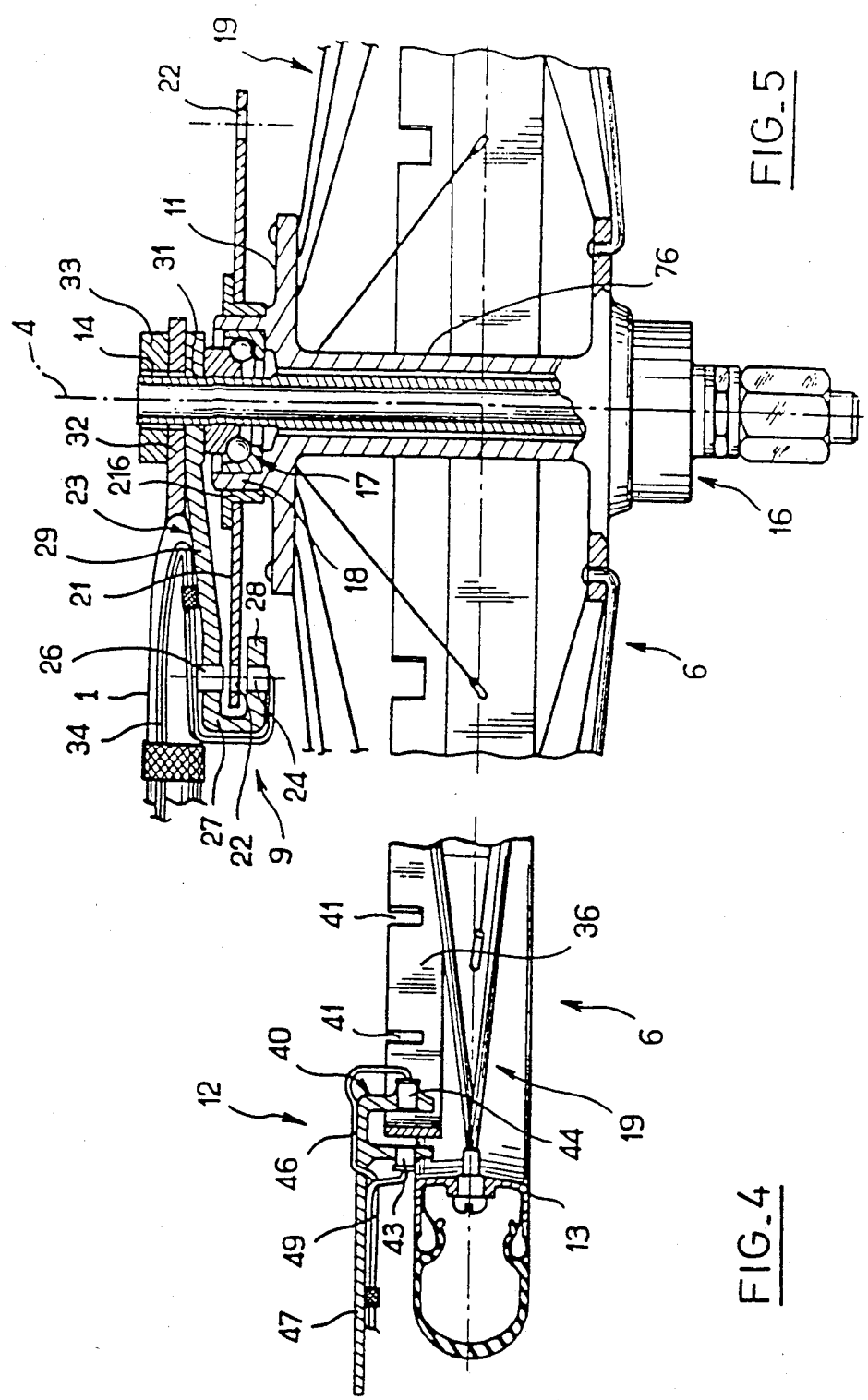

METHOD AND DEVICE FOR MEASURING THE TORQUE TRANSMITTED BY THE DRIVING WHEEL OF A CYCLE AND A CYCLE EQUIPPED WITH SAID DEVICE

BACKGROUND OF THE INVENTION

1. Field of the Invention

This invention relates to a method for measuring the torque transmitted by the driving wheel of a cycle and in particular the driving wheel of a bicycle.

A further object of the invention is to provide a device for the practical application of said method.

The present invention is also directed to a cycle equipped with said device.

2. Description of the Prior Art

In a known device of the type indicated in the foregoing and already disclosed in French Pat. No. FR-A-2,394,790, a roller is applied under the pressure of a spring against the driving run of the drive chain of the bicycle. As the effort transmitted by the chain is higher, so the driving run of the chain tends to lift and compress the spring to a greater extent. There accordingly exists a rule of correspondence between the deflection of the spring and the effort transmitted by the driving run of the chain.

This device suffers from numerous disadvantages. Prominent among these are its substantial weight and the fact that it provides inaccurate indications by reason of parasites corresponding to vibrations of the chain during operation. The effort measured is the effort transmitted by the chain which, at equal value, can correspond to different torques on the driving wheel if the bicycle is equipped with a gear-changing device. Moreover, the known device introduces friction on the chain.

German Pat. No. DE 31 50 149 describes a bicycle equipped with a torque-measuring device in which the detection elements can be placed at different locations. However, except for examples of construction corresponding in all cases to localization of the detection elements at the hub of the driving rear wheel, the last-mentioned patent specification makes reference solely to the possibility of mounting a recording instrument on the pedals or pedal cranks or else on the drive chain or the elements associated with this latter (front drive sprocket or rear driven sprocket). However, the cited patent (No. DE 31 50 149) fails to provide any information on practical solutions which may be adopted in the different cases thus contemplated.

It is only in the case of localization at the hub of the driving wheel that the aforementioned patent specification makes any definite suggestions. However, the solutions contemplated are both complex and costly since they involve the use of a hub of special design having two separate portions, namely a "driving portion" and a "driven portion" between which an elastic coupling element can be interposed. The measuring system is provided with means for detecting relative angular positions of each of the two portions thus provided on the hub. However, by reason of the very close proximity of these two portions, the angular differences are of very small value, which does not make it possible to carry out accurate measurements.

For these reasons, the object of the present invention is to propose a method, a device and a cycle in which measurement of torque or of a quantity related to torque is performed in a simple and accurate manner without entailing any modification of certain constituent elements of the cycle itself.

SUMMARY OF THE INVENTION

According to a first aspect of the invention, a method is provided for measuring the torque transmitted by the driving wheel of a cycle or a mechanical quantity which is a function of said torque and consists in measuring the angular difference between a driving portion and a driven portion of one of the rotating elements which perform a contributory role in the propulsion of the bicycle. More specifically, the method essentially consists in measuring the angular difference existing between a central region of the driving wheel and a peripheral region of said wheel by detecting the passage of two separate and distinct series of reference points carried respectively by the central region of the driving wheel and a peripheral region of said wheel, and in determining the torque or quantity related thereto by utilizing a predetermined rule of correspondence between the detected difference and the torque.

Thus the deformation of the driving wheel itself under the action of torque is detected and converted to a measurement of said torque. In this connection, it is worthy of note that it was not evident from the teachings of German Pat. No. DE 31 50 149 already cited to utilize the deformation of the driving wheel itself for measurement of torque, taking account of the fact that this patent specification merely contemplated the measurement of the angular difference existing between two separate and distinct portions of the hub of a wheel of this type by adopting a special arrangement which permitted a certain freedom of angular displacement between these two portions. In consequence, an expedient of this nature could not in any way be considered as suggesting the solution which is proposed in the method according to the invention and which consists in detecting the deformation existing between the central portion of the wheel and the peripheral portion of this latter. There was in any case no a priori evidence that deformation of the driving wheel is sufficient to allow the possibility of deducing the value of transmission torque from this deformation in a reliable and accurate manner.

In point of fact, the solution which is realized by means of the method in accordance with the invention has the advantage of detecting an angular difference between the central region of the wheel and its peripheral region and therefore between two regions which have a considerable relative spacing, thus permitting accurate measurement. Moreover, positioning of the detection elements does not give rise to any particular problem since some elements are located in the central region of the wheel whilst others are located in its peripheral region. Furthermore, since it is considered sufficient to determine a relative angular position, this can be achieved with light means which are not liable to introduce any friction. A further advantage is that there are no appreciable vibrations between the hub and the rim of a wheel in the circumferencial direction, with the result that measurements are practically not affected by parasites.

According to a second aspect of the invention, the device for carrying out the method described in the foregoing essentially includes first detecting means for detecting the angular position of the hub of the driving wheel about its axis, second detecting means for detecting the angular position of the rim of the driving wheel about its axis, means connected to the first and second detecting means and so designed as to deliver a signal which is representative of the angular difference between the rim and the hub about the axis of the driving wheel, and means for indicating the torque transmitted or the quantity related to said torque by utilization of the rule of correspondence between the angular difference and the transmitted torque.

According to a third aspect of the invention, the cycle which is equipped with the device aforesaid and the driving wheel of which is a wire-spoke wheel is distinguished by the fact that the driving wheel as seen in the axial direction has wire spokes which extend radially.

Spokes disposed in this manner permit relatively substantial angular differences between the hub and the rim of the wheel. Furthermore, even a very low torque produces an appreciable angular difference. The radial-spoke wheel in accordance with the invention constitutes a departure from the universally-adopted crossed-spoke technique. It might be expected that the radial-spoke wheel is distinctly less rugged. Tests have proved, however, that this is not the case in practice. This discovery appears to arise from the fact that all the spokes of the radial-spoke wheel take part in torque transmission to an equal extent whereas in a crossed-spoke wheel, the spokes directed from the hub obliquely towards the rear with respect to the direction of rotation are practically the only ones to transmit torque.

BRIEF DESCRIPTION OF THE DRAWINGS

FIG. 1 is a view in side elevation showing a bicycle in accordance with the invention.

FIG. 2 is a fragmentary view to a larger scale showing the driving wheel of the bicycle of FIG. 1 and the sensors.

FIG. 3 is a sectional view taken along line III—III of FIG. 2.

FIGS. 4 and 5 are views of the details IV and V of FIG. 3 respectively.

DETAILED DESCRIPTION OF THE INVENTION

Figure 6:
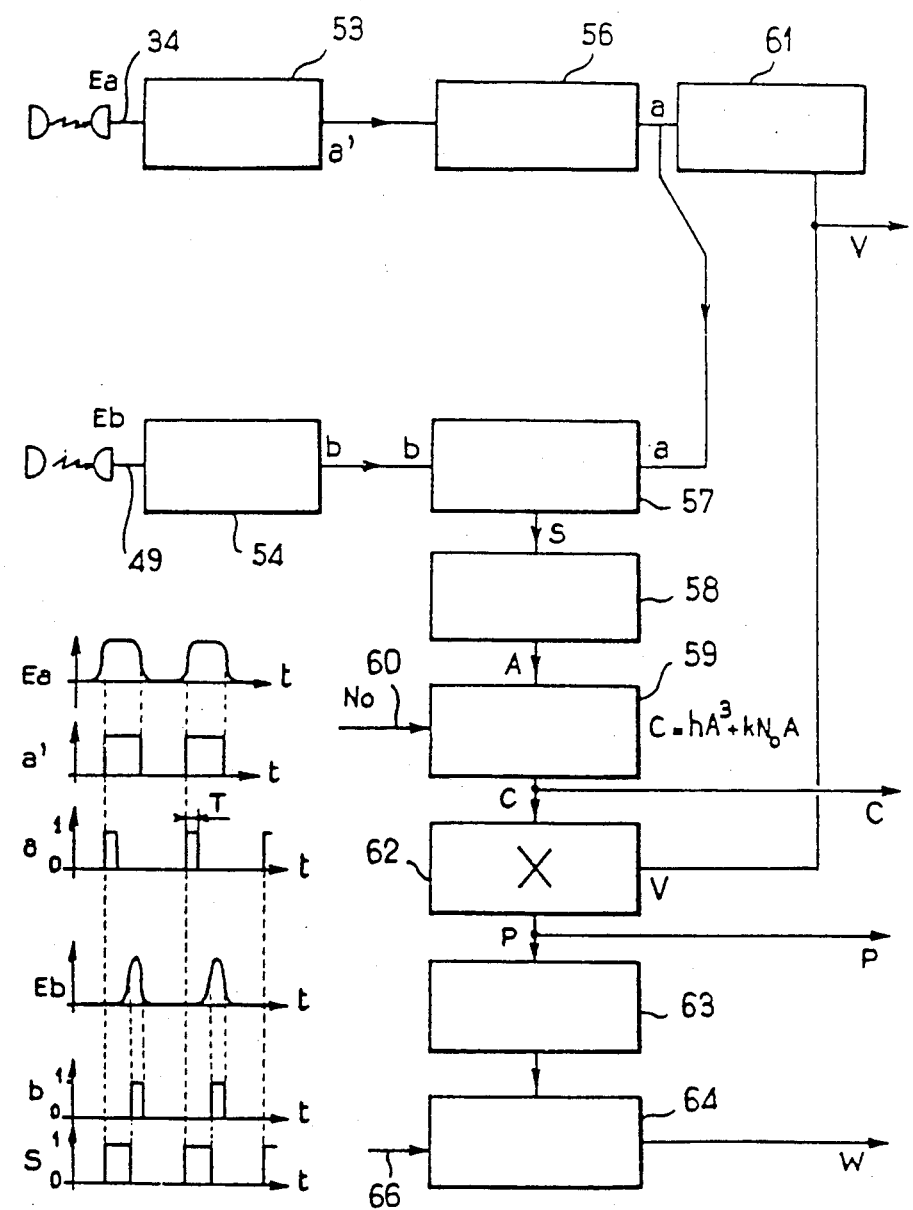
FIG. 6 is a view of the block diagram of the evaluation circuit provided on the bicycle of FIG. 1.

As shown in FIG. 1, the bicycle has a frame 1 in which is pivotally mounted a fork 2 for rotatably supporting a front wheel 3. A driving rear wheel 6 is rotatably supported by the frame 1 itself and driven in rotation about a horizontal axis 4 by means of a drive chain 7 from a pedal crank gear 8.

In accordance with the invention, the bicycle is provided with first detecting means 9 for detecting the angular position of a hub 11 of the wheel 6 about its axis 4 and with second detecting means 12 for detecting the angular position of a rim 13 of the wheel 6 about its axis.

As shown in FIG. 5, the hub 11 is supported on a hub shaft 14 by means of a free-wheel ball-bearing 16 on the side which is intended to receive the chain sprockets (not shown in the drawings) and by a ball-bearing 17 on the side opposite to the chain sprockets. The bearing 17 is mounted between the shaft 14 and a collar 18 formed on the hub 11 in the direction opposite to the spoke system as will hereinafter be described in greater detail.

The first detecting means 9 comprise an element or disk 21 having a central opening in which this latter receives a ring 21b to which it is attached. The ring 21b is forcibly fitted on the collar.

As shown in FIG. 2, the disk 21 is traversed by a series of openings 22 of circular shape and located in uniformly spaced relation in the vicinity of the peripheral edge of the disk 21 along a circle centered on the axis 4. The disk openings 22 consist of circular drilled holes which are all identical.

As shown in FIG. 5, the first detecting means 9 also include a sensor 23 having an infrared-radiation-emitting diode 24 and a photodiode 26 mounted in oppositely-facing relation on each side of the disk 21 so that the disk openings 22 pass successively between said emitting diode and said photodiode during service, that is to say when the wheel 6 is rotating about the axis 4 together with the disk 21.

The diodes 24 and 26 are rigidly coupled together by means of a yoke 27 which is mounted astride the disk 21 and the arms 28 and 29 of which are directed radially towards the axis 4. The relatively short arm 28 is adapted to carry the diode 24 between the disk 21 and the spoke system 19. The other arm 29 is adapted to carry the diode 26 opposite to the face of the disk 21 which is remote from the spoke system 19. The end of the arm 29 is provided with an orifice 31 which is engaged on the axis 4 and clamped between the inner ring of the ball-bearing 17 and a terminal lug 32 of the frame 1, the entire assembly being locked in position by means of a nut 33 applied against the outer face of the lug 32. A four-wire connection 34 attached to the frame 1 and to the yoke 27 consists of two wires for supplying current to the infrared diode 24 and two wires for departure of the signal generated by the photodiode 26.

The second detecting means 12 include an element 36 or hoop having a generally cylindrical shape, an axis which coincides with the axis 4 and a diameter which is slightly smaller than the internal diameter of the rim 13. The hoop 36 is placed laterally against the spoke system 19 on the same side as the first detecting means 9. Along the annular edge adjacent to the spoke system 19, said hoop 36 is provided with tongues 37 which are applied against the inner face of the rim 13 by means of tubular spacer members 38. Screws 39 passed through the tongues 37 and the spacer members 38 are screwed in the rim 13 in order to secure the hoop 36 in rigidly fixed relation to the rim 13.

On the edge remote from the spoke system 19, the hoop 36 is provided with castellated recesses or notches 41 (as shown in FIG. 3) which are all identical and uniformly spaced about the axis 4. Moreover, the total number of notches 41 is equal to the total number of disk openings 22.

The detecting means 12 are provided in addition with a sensor 40 (FIG. 4) composed of an infrared-radiation-emitting diode 43 and a photodiode 44 placed in oppositely-facing relation respectively internally and externally of the hoop 36 in such a manner as to ensure that the notches 41 pass successively between them when the hoop 36 is driven in rotation about the axis 4 by the wheel 6. The diodes 43 and 44 are held in stationarily fixed relation to each other by means of a yoke 46, the side portion of said yoke which is remote from the spoke system 19 being mounted astride the hoop 36. The yoke 46 is carried by a support bracket 47 which is fixed on the saddle tube 48 of the bicycle (as shown in FIG. 1). A four-wire connection 49 attached to the support bracket 47 consists of two wires for supplying electric current to the infrared diode 43 and of two wires for departure of the signal generated by the photodiode 44.

As shown in FIG. 6, the signals Ea and Eb emitted respectively by the photodiodes 26 and 44 are substantially binary. Thus one level corresponds to the case in which a disk opening 22 and notch 41 are both located between the diode and the photodiode. The other level corresponds to the case in which the metal of the disk 21 or of the hoop 36 is located between the diode and the photodiode.

Each signal is delivered via the lines 34, 49 (represented schematically in FIG. 1) to an electronic casing 51 which is secured to the handlebar 52 of the bicycle and contains at least one electric battery or dry cell for general power supply to the device.

Within the casing 51, the substantially binary signals aforesaid are converted to rectangular-wave signals by means of a bistable multivibrator 53 and 54 respectively. Furthermore, the signal a' emitted by the bistable multivibrator 53 associated with the photodiode 26 is processed in a monostable multivibrator 56 which delivers at its output a binary signal a constituted by a rectangular peak having an invariable time-duration T, the leading edge of which coincides in time with the leading edge of the rectangular-wave signals a'.

The signal a generated by the monostable multivibrator 56 and the signal b generated by the bistable multivibrator 54 are each delivered to one input respectively of a phase shifter 57 which delivers a rectangular-wave binary signal S at its output. The leading edge and trailing edge of each half-wave of said signal S coincide in time respectively with the leading edge of a peak of the signal a and with the leading edge of the peak which, in the signal b, immediately follows in time the aforesaid peak of the signal a.

Thus at each period, the time interval during which the signal S is at level 1 corresponds to the time-lag of signal b with respect to signal a or a', that is, to the time-lag of signal Eb with respect to signal Ea or, in other words, to the time-lag of the notches 41 of the hoop 36 with respect to the openings 22 of the disk 21.

At the time of assembly, the hoop 36 is positioned angularly about the axis 4 so as to ensure that the signals Ea and Eb rise at the same time when the wheel is not subjected to any shearing stress in the circumferential direction or in other words when no torque is transmitted. Accordingly, the time interval during which the signal S is at level 1 in each period indicates the relative angular difference existing between the rim and the hub of the wheel with respect to the reference position corresponding to a transmitted torque equal to 0.

The signal S is delivered to the input of an integrator 58, the analog output A of which is proportional at each instant to the time interval during which the signal S is at level A during each period. The signal A is therefore representative of the angle of relative displacement which exists between the rim and the hub of the wheel 6 with respect to the aforesaid reference position.

The signal A is delivered to the input of a computer 59 and this latter generates an analog signal C which is representative of the torque transmitted by the wheel 6 by utilizing a rule of correspondence between said torque and the angular difference A. In the example considered, this rule gives the torque C as a function of the variable A by means of the following function of the third degree:

$$C = hA^3 + kN_0 A$$

where $N_0$ is the no-load tension of the spokes of the system 19.

The description given hereinafter will show how the values h and k are determined and, more generally, will show how to construct a wheel which satisfies this rule of correspondence.

The output C of the computer 59 can be directly utilized for operating a device which serves to display the value of the torque transmitted by the driving wheel 6.

Furthermore, the output a of the monostable multivibrator 56 is delivered to the input of an integrator 61, the analog output V of which is proportional to the instantaneous speed of rotation of the wheel 6 about its axis 4 and consequently to the instantaneous speed of travel of the bicycle. This signal is obtained by producing at each instant the time integral of the signal a from an instant which precedes by an invariable period of time the instant at which the result is produced.

The signal C on the one hand and the signal V which is proportional to the speed of rotation of the wheel 6 on the other hand are each directed to one of the inputs of an analog multiplier 62, the analog output P of which is representative of the power transmitted by the driving wheel 6 (it is recalled that the power is equal to the product of the torque multiplied by the speed of rotation). The signal P can be directly employed for controlling display of the power developed by the cyclist at the rear wheel.

The signal V can in turn be directly utilized for controlling display of the rate of travel of the bicycle.

Furthermore, the signal P is delivered to the input of a voltage/frequency converter 63, the output signal of which is delivered to the input of a counter 64 which, by totalizing the number of pulses received from a predetermined instant at which a zero-reset has been performed by means of a specific control device 66, delivers at its output a signal W for initiating display by a device for summing the energy transmitted by the wheel 6.

In regard to the mode of calculation of this energy, it is recalled that the energy produced during an elementary time interval dt is equal to the product of the power P and the elementary time interval dt.

As shown in FIG. 1, the front wheel 3 of the bicycle is of a conventional crossed-spoke type. In other words, instead of appearing to be directed radially when the wheel is observed in an axial direction, the spokes of the wheel are inclined in particular with respect to the axial planes which pass through their ends. Starting from the hub 67 of the wheel 3, a certain number of spokes 68 are forwardly inclined with respect to the direction 69 of rotation of the wheel 3 whilst other spokes 71 which cross the spokes 68 are rearwardly inclined with respect to the direction 69.

In accordance with an important feature of the invention, the spoke system 19 of the driving rear wheel 6 is of a special type in which the spokes 72 appear to be directed radially when observing the wheel 6 in the axial direction. From FIG. 3, it is apparent that the direction of the spokes is not entirely radial. More particularly, the radially outer ends of the spokes 72 are all secured to the rim 13 along an ideal common circle 73. The radially outer ends of the spokes 72 are uniformly distributed along the circle 73. Starting from this circle, the spokes are divided into two opposite conical layers disposed symmetrically on each side of the central plane of the wheel which passes through the circle 73. At their radially inner end, the spokes 72 are attached to either of two flanges 74 provided on the hub 11 at both ends of a central tube 76 which surrounds the shaft 14 between the bearings 16 and 17. Spokes 72 forming part of each of the two layers are disposed in alternate succession along the rim 13.

It is worthy of note that a wheel 6 provided with spokes in accordance with this arrangement can be constructed from a rim, hub and spokes which could be suitably employed for the construction of a wheel 3. The only difference in assembly lies in the fact that the spokes are successively disposed in the same order at their radially inner ends and at their radially outer ends.

A wheel of this type satisfies the following relation which can be proved mathematically and verified experimentally with an error of only a few %:

$$C = hA^3 + kN_oA \qquad (1)$$

where:
C is the torque in N.m;
A is the angular difference in degrees between the rim and the hub of the wheel with respect to the reference position;
$N_o$ is the no-load tension of the spokes expressed in N;

$$h = \frac{n\eta^3 R^2 r^2 ES}{11\ 664.10^3 (R-r)^3};$$

$$k = \frac{n\eta Rr}{180(R-r)}.$$

In the expressions just given:
n is the number of spokes;
R is the radius of the rim or more precisely the distance between the radially outer point of attachment of the spokes 72 and the axis of the wheel;
r is the distance between the radially inner point of attachment of the spokes and the axis of the wheel;
E is the Young's modulus;
S is the cross-sectional area of each spoke.

In one example of construction in which a rim, a hub and spokes of a commercially available type were employed, the following values were obtained:
h = 0.163
k = 0.0224.

This function of the third degree corresponds the high sensitivity of the wheel to low or very low torques and to good resistance of the wheel to deformations beyond a predetermined threshold value of approximately 6°, for example. Sensitivity of the device to low values of torque secures the advantage of providing an effective measurement of such values. The fact that the wheel cannot readily overstep a predetermined deformation threshold is clearly conducive to mechanical strength and has the further advantage of preventing saturations in the electronic portion of the device. The angular difference between the successive rectangular notches 41 is chosen so as to be substantially greater than the maximum angular deformation which is likely to be encountered in practice.

The mechanical tension of the spokes can be chosen over a fairly wide range between 100 and 400 Newton, for example. The computer has an input 60 for entering the values of $N_o$.

The operation of the bicycle as well as the method in accordance with the invention will now be described.

In the state of rest or in other words when no torque is transmitted, the spokes are in a radial position (when the wheel is observed axially) under the action of their tension. The relative angular position of the disk 21 and of the hoop 36 is such that the disk openings 22 and the rectangular notches 41 initiate simultaneously the rise of the signals $E_a$ and $E_b$ respectively, with the result that the signal S is continuously at the level 0 and the computer indicates the value 0 in the case of C.

When the chain 7 transmits torque to the wheel 6, the hub 11 tends to rotate at a higher speed than the rim 13 whilst the spokes assume an inclined position with respect to their initial radial position. The relative angular displacement between hub and rim is detected by the phase-shifter 57 and the integrator 58. The computer determines the torque from formula (1) given above.

It is apparent from the foregoing that, in order to detect the angular difference, it is necessary to detect the passage of the reference points 22 associated with the hub 11 and of the reference points 41 associated with the rim 13. The angular difference or divergence is deduced from the time-delay of the reference points 41 with respect to the reference points 22.

In addition, detection of passage of the reference points 22 is utilized for the purpose of measuring the speed of rotation V of the wheel.

It has been seen that quantities such as power P and energy W related to velocity V and to torque C are also computed.

It would also be possible to compute quantities related solely to torque such as mean torque, for example, or quantities related solely to speed such as average speed, for example.

The invention is applicable to different wheels as well as to other types of vehicles and especially "self-propelled" motor bicycles or mopeds.

What is claimed is:
1. A method for measuring the torque transmitted by the driving wheel of a cycle or a mechanical quantity which is a function of said torque, which consists in measuring the angular difference between a driving portion and a driven portion of one of the rotating elements which perform a contributory role in the propulsion of the cycle, wherein the angular difference existing between a central region of the driving wheel and a peripheral region of said wheel is measured by detecting the passage of two separate and distinct series of reference points carried respectively by the central region of the driving wheel and a peripheral region of said wheel and the torque or quantity related thereto is determined by utilizing a predetermined rule of correspondence between the detected difference and the torque.

2. A method according to claim 1, wherein detection of the passage of at least a certain number of reference points is utilized for additionally measuring the speed of rotation of the wheel and/or at least one quantity which is related thereto.

3. A device for measuring the torque transmitted by the driving wheel of a cycle or a mechanical quantity which is a function of said torque, wherein said device includes first detecting means for detecting the angular position of a central region of the driving wheel about its axis, second detecting means for detecting the angular position of a peripheral region of the driving wheel about its axis, a phase shifter and integrator connected to the first and second detecting means for delivering a signal which is representative of the angular difference between the central region and the peripheral region about the axis of the driving wheel, and computing means for determining the transmitted torque or the quantity related thereto by utilization of the rule of correspondence between the angular difference and the transmitted torque.

4. A device according to claim 3, wherein each of the first and second detecting means includes on the one hand an element which is intended to be attached to the driving wheel and has at least one reference point and on the other hand a sensor which can be attached to a frame in a position adjacent to a portion of the path followed by said reference point during rotation of the wheel and which is adapted to deliver a substantially binary signal, the level of which is representative of the passage of said reference point in front of said sensor.

5. A device according to claim 4, wherein said element is provided with at least one opening which constitutes a reference point.

6. A device according to claim 4, wherein the sensor of each of the first and second detecting means is of the photoelectric type.

7. A device according to claim 4, wherein means are further provided for determining from the substantially binary signal the speed of rotation of the driving wheel and/or a quantity related thereto.

8. A device according to claim 3, wherein the driving wheel of the cycle is included in said device and satisfies a rule of correspondence which gives the transmitted torque as a function of the angular difference and is at least of the third degree.

9. A device according to claim 3, wherein the driving wheel of the cycle is included in said device and is provided with wire spokes extending radially when observed in the axial direction.

10. A cycle equipped with a device according to claim 3 in which the driving wheel is a wire-spoke wheel, wherein the driving wheel is provided with wire spokes which extend axially when observed in the axial direction.

* * * * *